US008092808B2

(12) United States Patent
Agin et al.

(10) Patent No.: US 8,092,808 B2
(45) Date of Patent: Jan. 10, 2012

(54) **OVO VACCINATION OF *CAMPYLOBACTER* IN AVIAN SPECIES**

(75) Inventors: Tonia Sue Agin, Schoolcraft, MI (US); Everett L. Rosey, Schoolcraft, MI (US); Frederick H. Weber, Mattawan, MI (US)

(73) Assignee: Pfizer, Inc., New York, NY (US)

( * ) Notice: Subject to any disclaimer, the term of this patent is extended or adjusted under 35 U.S.C. 154(b) by 406 days.

(21) Appl. No.: 10/578,162

(22) PCT Filed: Nov. 22, 2004

(86) PCT No.: PCT/IB2004/003806
§ 371 (c)(1), (2), (4) Date: Nov. 29, 2006

(87) PCT Pub. No.: WO2005/053737
PCT Pub. Date: Jun. 16, 2005

(65) Prior Publication Data

US 2007/0116722 A1 May 24, 2007

Related U.S. Application Data

(60) Provisional application No. 60/526,681, filed on Dec. 3, 2003.

(51) Int. Cl.
*A61K 39/02* (2006.01)

(52) U.S. Cl. .................. 424/234.1; 424/93.4; 435/252.1

(58) Field of Classification Search ........................ None
See application file for complete search history.

(56) References Cited

U.S. PATENT DOCUMENTS

| | | | | |
|---|---|---|---|---|
| 4,040,388 | A | 8/1977 | Miller | |
| 4,469,047 | A | 9/1984 | Miller | |
| 4,593,646 | A | 6/1986 | Miller | |
| 4,681,063 | A | 7/1987 | Hebrank | |
| 5,977,081 | A | 11/1999 | Marciani | |
| 6,231,871 | B1 | 5/2001 | Coloe | |
| 6,410,222 | B1 * | 6/2002 | Yokogawa et al. | 435/5 |
| 6,440,408 | B2 | 8/2002 | Thoma | |
| 6,491,910 | B1 | 12/2002 | Schneit | |
| 2002/0187162 | A1 | 12/2002 | Geary et al. | |

FOREIGN PATENT DOCUMENTS

| | | | |
|---|---|---|---|
| WO | WO 98/56413 | A1 | 12/1998 |
| WO | WO 99/43348 | A1 | 9/1999 |
| WO | WO 03/030932 | A1 | 4/2003 |

OTHER PUBLICATIONS

Guerry, Patricia, et al., "Development and Characterization of Reca Mutants of *Campylobacter jejuni* for Inclusion in Attenuated Vaccines," Infection and Immunity, American Society for Microbilogy, Feb. 1994, p. 426-432.
Noor, S.M., et al., "In ovo oral vaccination wipth *Campylobacter jejuni* establishes early development of intestinal immunity in chickens," British Poultry Science, 1995, 36(4): 563-573.
Rice, Brandt E., et al., "*Campylobacter jejuni* in broiler chickens: colonization and humoral immunity following oral vaccination and experimental infection", Vaccine 15(17-18), 1997, pp. 1922-1932.
Ziprin, Richard L., et al, "Inoculation of Chicks with Viable Non-Colonizing Strains of *Campylobacter jejuni*: Evaluation of Protection Against a Colonizing Strain," Current Microbiology 44(3), 2002, pp. 221-223.
Ziprin, Richard L., et al., "Effect of mutations in *Campylobacter jejuni* genes on cecal colonization, and liver invasion, when given in ovo or on day-of hatch,"—Abstract, Poultry Science, vol. 78, Suppl. 1, 1999, p. 39.
G.C. Mead, "Factors affecting intestinal colonization of poultry by *Campylobacter* and role of microflora in control", World Poultry Science Journal, vol. 58, 2002, 169-178.
Smith, "Observations on the flora of the alimentary tract of animals and factors affecting its composition", Journal of Pathology and Bacteriology (1965) 89:95-122.
Barnes et al., "The intestinal flora of the chicken in the period 2 to 6 weeks of age with particular reference to the anaerobic bacteria", British Journal of Poultry Science (1972) 13:311-326.
Ricks et al., "In ovo vaccination technology", Advances in Veterinary Medicine (1999) 41:495-515.
Stas et al., "Experimental infection of chickens with *Campylobacter jejuni*: strains differ in their capacity to colonize the intestine", Avian Pathology (1999) 28:61-64.
Muir et al., "Immunity, vaccination and the avian intestinal tract", Developmental and Comparative Immunology (2000) 24:325-342.

* cited by examiner

*Primary Examiner* — Jennifer Graser
(74) *Attorney, Agent, or Firm* — Brandon Boss; Michael J. Moran; E. Victor Donahue

(57) ABSTRACT

The present invention provides a method of inducing an immune response against *Campylobacter* in an avian species, especially a domesticated avian species such as chicken, turkey, duck, goose and quail, by administering, in ovo, live cells of *Campylobacter*.

19 Claims, No Drawings

OVO VACCINATION OF *CAMPYLOBACTER* IN AVIAN SPECIES

CROSS-REFERENCE TO RELATED APPLICATIONS

This Application is filed under 35 USC 371 as a US National Stage Patent Application of PCT/IB2004/003806, filed Nov. 22, 2004 under 35 USC 363, which claims the benefit under 35 USC 119(e)(1) of U.S. Provisional Patent Application No. 60/526,681, filed Dec. 3, 2003 under 35 USC 111(b), the entire disclosures of which are incorporated by reference herein.

FIELD OF THE INVENTION

This invention relates to methods of inducing an immune response in an avian species against *Campylobacter* by administering, in ovo, live *Campylobacter* cells.

BACKGROUND OF THE INVENTION

Consumption of poultry contaminated with *Campylobacters* has been implicated as a major source of human infection. Therefore, removal of these organisms from the poultry food chain has been a significant objective of *Campylobacter* research.

*Campylobacters* typically grow and colonize in the avian gut environment. Colonization has been reported in chickens, ducks, pigeons, quail, ostriches and turkeys. Colonization of poultry does not result in disease but is commensal in nature.

The use of a competitive exclusion culture to exclude *Salmonella* or *Campylobacter* from the digestive tract of a bird has been described in U.S. Pat. No. 6,491,910. The efficacy of this method against *Campylobacter* appears variable. In ovo vaccination with heat killed cells of *Campylobacter jejuni* has been described by Noor et al. (*British Poultry Science,* 1995. 36(4): 563-73) and by S. Noor (*Jurnal Ilmu Ternak Dan Veteriner,* 1998. 3(4): 264-269). In ovo immunization of chickens with flagellin and whole cell protein antigens of *Campylobacter jejuni* has also been reported by S. Noor et al. (*Jurnal Ilmu Ternak Dan Veteriner,* 2000. 5(2): 119-124). Efforts have also been made in order to identify the genes involved in colonization (Ziprin et al., Abstracts, Poultry Science Association meeting, Aug. 8-11, 1999, Springdale, Ark.). See also, Rice, 1997, *"Campylobacter jejuni* in broiler chickens: colonization and humoral immunity following oral vaccination and experimental infection", *Vaccine* 15 (17-18): 1922-1932, wherein killed *Campylobacter* cells are administered; and Ziprin et al, 2002, *Current Microbiology* 44(3): 221-223, wherein chicks were vaccinated post-hatch with viable but non-colonizing strains.

Prior to the present invention, there has been no effective immunization strategy that employs in ovo administration with live *Campylobacter* cells.

SUMMARY OF THE INVENTION

The present invention provides a method of inducing an immune response in an avian species against *Campylobacter* by administering, in ovo, live cells of *Campylobacter.*

According to the present invention, live cells of *Campylobacter* can be safely administered to any avian species for the purpose of inducing an immune response against *Campylobacter*, especially a domesticated avian species such as chicken, turkey, duck, goose and quail.

*Campylobacter* species suitable for use in the present method include, but are not limited to, *Campylobacter jejuni, Campylobacter coli, Campylobacter lari*, or a combination thereof.

The cells of *Campylobacter* can be wild type cells or cells of *Campylobacter* that have been genetically modified to contain one or more mutations in the genome, or to contain a desirable heterologous sequence.

Preferably, the cells are combined with a veterinary-acceptable carrier prior to administration and are administered in an amount that is effective to induce an immune response in the avian species developed from the treated egg, preferably in an amount of at least about $5\times10^5$, and more preferably, of at least about $1\times10^6$ live cells.

DETAILED DESCRIPTION OF THE INVENTION

It has been surprisingly found in accordance with the present invention that live cells of *Campylobacter* can be safely administered in ovo, to eggs of an avian species, which results in effective colonization and induces an immune response in the avian species against *Campylobacter.*

Accordingly, the present invention provides a method of inducing an immune response in an avian species against *Campylobacter* by in ovo administration of live cells of *Campylobacter.*

As used herein, the term "avian species" or "bird" is meant to include any avian species, including a domestic or a game bird, e.g., chicken, turkey, duck, goose, or quail. Preferably, live cells of *Campylobacter* are administered to eggs of a domesticated bird raised for commercial production of eggs or meat, such as a domesticated chicken, turkey, duck, goose and quail.

The term "*Campylobacter*" refers to any *Campylobacter* species or any strain of a *Campylobacter* species, including *Campylobacter jejuni, Campylobacter coli, Campylobacter lari. Campylobacter* strains suitable for use in the present method include *C. jejuni* UA535 and *C. jejuni* 81-176, as well as the following mutant strains: *C. jejuni* CsrA (mutated within gene Cj1103, a csrA homolog), *C. jejuni* HspR (Cj1230), *C. jejuni* HtrA (Cj1228c), *C. jejuni* Dps (Cj1534c), *C. jejuni* flbA (Cj0822c), *C. jejuni* Pnp (Cj1253), and *C. jejuni* SurE (Cj0293).

Both wild type and mutant strains of a *Campylobacter* species can be used in the method of the present invention, including strains that have been genetically engineered and contain one or more mutations in the genome. The capacity of a mutant *Campylobacter* strain in colonization and induction of an immune response in an avian species can be determined following the techniques described in the examples hereinbelow or techniques known to those skilled in the art.

In a preferred embodiment, the *Campylobacter* strain employed in the method of the present invention has been genetically engineered to contain a heterologous polynucleotide sequence. The heterologous sequence can be transferred into the *Campylobacter* strain via a plasmid, phage or cosmid vector by various means such as conjugation, electroporation, or transformation. Other methods such as transduction are also suitable, wherein the recombinant DNA in the form of a transducing phage or cosmid vector is packaged within a phage. Once the recombinant polynucleotide is in the carrier *Campylobacter* strain, it may continue to exist as a separate autonomous replicon or it may insert into the *Campylobacter* chromosome and be reproduced along with the chromosome during cell division.

According to the present invention, the heterologous polynucleotide sequence can encode an antigen from an organism, such as a virus, bacterium or parasite, that causes disease in bird or that causes food-borne illness in humans upon consumption of a bird contaminated with the organism. Administration of live cells of genetically engineered *Campylobacter* containing such heterologous sequence can induce an immune response in the avian species against both *Campylobacter* and the pathogenic organism. Examples of such pathogenic organisms include *Salmonella, Escherichia coli, Eimeria, Clostridium*, infectious bursal disease virus.

The heterologous polynucleotide sequence can also encode a protein essential in colonization of domesticated birds by *Campylobacter*. Proteins known to be essential in colonization of *Campylobacter* include, e.g., the gene products of dnaJ and cadF.

Additionally, the heterologous polynucleotide sequence can encode a protein or peptide that stimulates the immune system of bird. Examples of proteins or peptides that stimulate the immune system of birds include, e.g., cholera toxin or *E. coli* heat labile toxin.

Moreover, the heterologous polynucleotide sequence can itself enhance the growth or feed efficiency of a domesticated bird, or can encode a protein or peptide that enhances the growth or feed efficiency of a domesticated bird. Examples of such molecules or proteins include epidermal growth factor, insulin-like growth factor, interleukins, and antimicrobial peptides.

According to the present invention, a *Campylobacter* species is cultured by standard methods known to those skilled in the art and live cells of such *Campylobacter* are collected for in ovo administration to eggs of an avian species. Live cells of more than one *Campylobacter* species can be combined for in ovo administration.

In addition to *Campylobacter* cells, a veterinary-acceptable carrier can also administered. Preferably, *Campylobacter* cells and a veterinary-acceptable carrier are both administered in ovo, either together or separately. Alternatively, a veterinary-acceptable carrier can be administered to the bird any time post-hatch in feed or water, or by aerosol spray. The live *Campylobacter* cells administered, whether with or without a veterinary-acceptable carrier, are free of neutralizing factors, such as neutralizing antibodies or fragments of antibodies, as described in U.S. Pat. No. 6,440,408.

The term "a veterinary-acceptable carrier" includes solvents, dispersion media, coatings, adjuvants, stabilizing agents, diluents, preservatives, antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others.

Adjuvants suitable for use in the present method include but are not limited to: mineral gels, e.g., aluminum hydroxide; surface active substances such as lysolecithin; glycosides, e.g., saponin derivatives such as Quil A or GPI-0100 (U.S. Pat. No. 5,977,081); cationic surfactants such as DDA, pluronic polyols; polyanions; non-ionic block polymers, e.g., Pluronic F-127 (B.A.S.F., USA); peptides; mineral oils, e.g. Montanide ISA-50 (Seppic, Paris, France), carbopol, Amphigen (Hydronics, Omaha, Nebr. USA), Alhydrogel (Superfos Biosector, Frederikssund, Denmark) oil emulsions, e.g. an emulsion of mineral oil such as BayolF/Arlacel A and water, or an emulsion of vegetable oil, water and an emulsifier such as lecithin; alum, cholesterol, rmLT, cytokines and combinations thereof. The immunogenic component may also be incorporated into liposomes, or conjugated to polysaccharides and/or other polymers for use in a vaccine formulation. Additional substances that can be included in a product for use in the present methods include, but are not limited to one or more preservatives such as disodium or tetrasodium salt of ethylenediaminetetracetic acid (EDTA), merthiolate, and the like. Immunostimulants which enhance the immune system's response to antigens may also be included in a product. Examples of suitable immunostimulants include cytokines such as IL-12 or IL-2, or stimulatory molecules such as muramyl dipeptide, aminoquinolones, lipopolysaccharide, and the like. The adjuvant can be combined with live cells of *Campylobacter* prior to in ovo administration, or can be administered independently any time after hatching by way of feed, water or aerosol spray, provided to the bird.

The live cells are administered at a dose effective to induce an immune response against *Campylobacter* in the avian species developed from the treated egg. The amount of live cells of *Campylobacter* that is effective to induce an immune response, or "the immunizing effective amount", may vary, depending on the particular species or strains of *Campylobacter* used in the administration and the species of bird being immunized. Generally speaking, at least about $5\times10^5$ live cells should be administered to be effective in inducing an immune response. More preferably, at least about $1\times10^6$ live cells of *Campylobacter* are administered.

By "inducing an immune response" is meant that the live cells of *Campylobacter* administered to an egg induce an immune response in the bird developed from the egg, which in turn provides some degree of protection to the bird against colonization of a *Campylobacter* species, which can be the same as, or different from, the *Campylobacter* species used in the in ovo administration.

An immune response induced by in ovo administration of live cells of *Campylobacter* can be a cellular immune response mediated primarily by cytotoxic T-cells, or a humoral immune response mediated primarily by helper T-cells, which in turn activates B-cells leading to antibody production, or the combination of a cellular immune response and a humoral immune response.

According to the present invention, one or more additional immunogens can be included in the administration in ovo. Such immunogens include antigens derived from viruses, e.g. avian infectious bronchitis virus, avian infectious bursal disease virus, avian encephalomyelitis virus, egg drop syndrome virus, influenza virus, reovirus, adenovirus, hydropericardium syndrome virus, among others; antigens derived from bacteria, e.g., *Haemophilus paragallinarum, Salmonella typhimurium, S. enteritidis, S. pullori, S. gallinarum, S. choleraesuis, E. coli, Clostridium* spp., *Mycoplasma* spp., *enterococcus*, among others; and antigens derived from protozoan, e.g. *Eimeria tenella, E. maxima, E. acervulina, E. brunetti, E. necatrix*, among others.

By "in ovo administration" is meant administration to eggs of an avian species, preferably eggs in the fourth quarter of incubation. That is, for chicken eggs, the administration is conducted preferably on about the fifteenth to nineteenth day of incubation, and more preferably on about the eighteenth day of incubation. For turkey eggs, the administration is conducted preferably on about the twenty-first to twenty-sixth day of incubation, and more preferably on about the twenty-fifth day of incubation.

The administration can be conducted by any method which results in the introduction of live cells of *Campylobacter* into an egg through the shell. A preferred method of administration is by injection. The injection can be made at any site of an egg, so long as the injection does not damage the tissues or organs of the embryo, or the extraembryonic membranes surrounding the embryo. The injection can be achieved by using any one of the well-known egg injection devices, such as a conventional hypodermic syringe fitted with a needle of about 18 to 22 gauge, or a high speed automated egg injection system as described in U.S. Pat. Nos. 4,681,063, 4,040,388, 4,469,047, and 4,593,646.

The present invention is further illustrated by the following non-limiting examples.

EXAMPLE 1

Broiler chicken eggs were injected in ovo on day 18 of incubation with $10^6$ colony forming units (CFU) of *Campylobacter jejuni* UA535. This is a wild type, unmodified strain of *C. jejuni*, originally isolated from a human clinical case of campylobacteriosis. A second group of eggs remained uninoculated until the day of hatch, at which time the chicks in this group were inoculated per os with $10^6$ CFU *C. jejuni* UA535. At hatch, the number of live chicks and unhatched eggs in each treatment were recorded and all chicks were placed on litter with 3 replicate pens of twenty birds per treatment.

In ovo inoculation had no impact on hatch rate, since 97.5% of uninoculated eggs and 98.8% of inoculated eggs hatched. Both groups were similar in weight at hatch and gained weight at a similar rate throughout the study. The two routes of administration of *C. jejuni* to broiler chicks resulted in equivalent colonization both in terms of the number of birds colonized and the number of *C. jejuni* per gram of cecal contents. No signs of clinical significance were observed in any of the birds. These data indicate that in ovo inoculation of broiler chicks with *C. jejuni* is as safe as per os inoculation.

The geometric mean antibody titer in response to in ovo inoculation was at least as great as, if not greater than, the titer resulting from per os inoculation at day of hatch. Therefore, not only can wild type *C. jejuni* UA535 be safely administered in ovo to broiler chicks, but administration by this route results in robust colonization and immune response.

EXAMPLE 2

To demonstrate that colonization after in ovo inoculation with *C. jejuni* is not unique to strain UA535, colonization of birds by another human clinical isolate, *C. jejuni* 81-176, was evaluated. Groups of broiler eggs were injected on Day 18 of embryo incubation with $1.8\times10^5$ or $1.4\times10^7$ CFU of *C. jejuni* 81-176. A third group of eggs remained uninoculated. At hatch, a group of chicks from the uninoculated eggs were retained as uninoculated control birds, and a second group of chicks from these eggs were given $8.3\times10^6$ CFU of *C. jejuni* 81-176 orally.

The data set obtained demonstrated that in ovo administration of *C. jejuni* strain 81-176 is at least as effective at colonizing broiler chicks as oral administration on the day of hatch.

EXAMPLE 3

On day 18 of embryo incubation, a group of broiler chicken eggs were inoculated in ovo with $7\times10^7$ CFU of *C. jejuni* CsrA. This strain has a mutation in CsrA, a protein involved in global regulation of carbon storage. A second group of eggs were retained as uninoculated controls. At hatch, a group of chicks from the uninoculated eggs were given $3\times10^8$ CFU of *C. jejuni* CsrA orally. Another group of chicks hatched from uninoculated eggs were retained as controls.

The results indicated that the mutant *C. jejuni* strain colonized all of the birds when administered in ovo, yet colonized only 3 out of 6 birds when given orally. Also, the mutant was able to fully colonize birds and induce an antibody response when administered in ovo, but appeared to be less effective at colonizing birds when given by the oral route on the day of hatch.

EXAMPLE 4

On day 18 of embryo incubation, groups of broiler chicken eggs were inoculated in ovo with $9\times10^6$ CFU of *C. jejuni* HspR, $8\times10^7$ CFU of *C. jejuni* HtrA, or $6\times10^7$ CFU of *C. jejuni* Dps. The HspR strain has a mutation in a heat shock protein; the HtrA strain has a mutation in a serine protease gene; and the Dps strain is mutated in a gene involved in iron acquisition. Another group of eggs was retained as uninoculated controls. At hatch, groups of chicks from the uninoculated eggs were given $4\times10^6$ CFU of *C. jejuni* HspR, $1\times10^8$ CFU of *C. jejuni* HtrA, or $1\times10^8$ CFU of *C. jejuni* Dps orally. Another group of chicks hatched from uninoculated eggs was retained as controls.

The HspR mutant was undetectable in samples from birds inoculated per os, but half the birds given this strain in ovo were colonized with *C. jejuni*. The results indicate that this mutant was able to colonize broiler chicks after in ovo administration, but not after oral administration on the day of hatch. The other mutants readily colonized birds and induced an immunological response regardless of route of administration.

EXAMPLE 5

On day 18 of embryo incubation, groups of broiler chicken eggs were inoculated in ovo with $7.3\times10^7$ CFU of *C. jejuni* flbA, $1.1\times10^8$ CFU of *C. jejuni* Pnp, or $1.2\times10^8$ CFU of *C. jejuni* SurE. The FlbA strain is mutated in a gene encoding for a flagellar structural protein; the Pnp strain is mutated in a gene encoding for a nucleotidyltransferase; and the SurE strain is mutated in a gene encoding a phosphatase. Another group of eggs was retained as uninoculated controls. At hatch, groups of chicks from the uninoculated eggs were given $9.3\times10^7$ CFU of *C. jejuni* flbA, $1.6\times10^8$ CFU of *C. jejuni* Pnp, or $8\times10^7$ CFU of *C. jejuni* SurE orally. Another group of chicks hatched from uninoculated eggs was retained as controls.

The FlbA mutant demonstrated a transient colonization when given by the in ovo route, and this mutant appeared unable to colonize by the oral route. The Pnp mutant colonized birds effectively regardless of route of administration. The SurE mutant colonized birds effectively when administered by the in ovo route, but was unable to colonize birds when administered orally.

EXAMPLE 6

On Day 18 of incubation, a group of broiler chicken eggs were injected in ovo with $2\times10^6$ cells of wild-type *C. jejuni* strain UA535. A second group of eggs were maintained as uninoculated controls. At hatch, a group of birds from uninoculated eggs were inoculated per os with $2\times10^6$ cells of *C. jejuni* UA535. The remaining birds that hatched from uninoculated eggs were kept as controls. At 27 days post-hatch, half of the birds in each group were placed on medicated water containing 100 mg/L kanamycin to eliminate the immunizing *C. jejuni* strain. These infected/cleared birds would therefore be considered “immunized”.

At 34 days post-hatch, selected groups of birds were exposed to birds previously infected with *C. jejuni* CjM20, a strain genetically-modified to be resistant to kanamycin. This method allowed the spread of CjM20 from the infected birds to the “immunized” birds. By diagnostic means, it was possible to distinguish the strain CjM20 from the immunizing strain UA535 in the samples collected.

Non-immunized, non-medicated birds challenged with CjM20 were fully colonized by 41 days of age. Colonization was delayed somewhat by kanamycin treatment, with about half the birds colonized by Day 41. All of the non-immunized, medicated, challenged birds were fully colonized by 49 days of age. Both groups of immunized birds had reduced numbers of *C. jejuni* compared with their non-immunized counterparts. All recovered bacteria appeared resistant to kanamycin, indicating that the immunizing strain was eliminated by kanamycin treatment. Immunized, non-challenged birds remained free of *C. jejuni* throughout the study. Thus, immunization of broiler chicks against colonization with *C. jejuni* was at least as effective by the in ovo route as by the oral route.

What is claimed is:

1. A method of inducing a protective immune response in a bird against *Campylobacter jejuni*, comprising administering, in ovo, during the final quarter of incubation, an immunizing effective amount of live cells of *Campylobacter jejuni*, wherein said live cells are free of neutralizing antibodies or neutralizing antibody fragments.

2. The method of claim 1, wherein said bird is a domesticated bird.

3. The method of claim 2, wherein said domesticated bird is selected from the group consisting of a chicken, a turkey, and a duck.

4. The method of claim 1, wherein the live cells are wild type or have been modified genetically.

5. The method of claim 4, wherein a heterologous polynucleotide sequence has been introduced into the live cells of *Campylobacter jejuni.*

6. The method of claim 5, wherein said heterologous polynucleotide sequence encodes a protein essential in colonization of a domesticated bird by *Campylobacter jejuni.*

7. The method of claim 5, wherein said heterologous polynucleotide sequence encodes an antigen from a virus, bacteria, or parasite that causes disease in a domesticated bird.

8. The method of claim 5, wherein said heterologous polynucleotide sequence encodes an antigen from an organism that causes food-borne illness in humans.

9. The method of claim 5, wherein said heterologous polynucleotide sequence encodes a protein that enhances the growth or feed efficiency of a domesticated bird.

10. The method of claim 5, wherein said heterologous polynucleotide sequence encodes a protein that stimulates the bird's immune system.

11. The method of claim 1, further comprising administering a veterinary-acceptable carrier.

12. The method of claim 11, wherein said veterinary-acceptable carrier is combined with the live cells of *Campylobacter jejuni* prior to in ovo administration.

13. The method of claim 11, wherein said veterinary-acceptable carrier is administered to the bird in feed or water, or by aerosol spray, at any time after hatching.

14. The method of claim 12, wherein said veterinary-acceptable carrier is an adjuvant.

15. The method of claim 14, wherein said adjuvant has an immune-stimulating activity.

16. The method of claim 1, wherein live cells of *Campylobacter jejuni* are combined with at least one other immunogen selected from a viral, a bacterial or a protozoan immunogen.

17. The method of claim 13, wherein said veterinary-acceptable carrier is an adjuvant.

18. The method of claim 17, wherein said adjuvant has an immune-stimulating activity.

19. A method of inducing a protective immune response in a bird against *Campylobacter jejuni*, comprising administering, in ovo, during the final quarter of incubation, an immunizing effective amount of live cells of *Campylobacter jejuni*, wherein said live cells are free of neutralizing antibodies or neutralizing antibody fragments; and wherein said bird is then harvested for human food consumption.

* * * * *